United States Patent [19]

Möller

[11] Patent Number: 4,659,824

[45] Date of Patent: Apr. 21, 1987

[54] ACID ADDITION PRODUCTS OF N-GLYCIDYL COMPOUNDS

[75] Inventor: Hinrich Möller, Monheim, Fed. Rep. of Germany

[73] Assignee: Henkel Kommanditgesellschaft auf Aktien, Duesseldorf, Fed. Rep. of Germany

[21] Appl. No.: 643,611

[22] Filed: Aug. 23, 1984

[30] Foreign Application Priority Data

Aug. 25, 1983 [DE] Fed. Rep. of Germany ....... 3330640
Jul. 4, 1984 [EP] European Pat. Off. ......... 84107759.7

[51] Int. Cl.[4] .................. C07D 403/06; C07D 233/02; C07D 249/12; C07D 253/06
[52] U.S. Cl. ..................... 544/221; 544/302; 544/256; 548/264; 548/337; 548/301; 548/302; 548/308
[58] Field of Search .............. 548/264, 337, 301, 302, 548/308; 544/221, 302, 256

[56] References Cited

U.S. PATENT DOCUMENTS

4,377,694  3/1983  Giesecke et al. ............... 548/264
4,393,060  7/1983  Fischer et al. ................. 544/221

FOREIGN PATENT DOCUMENTS

0033503  8/1981  European Pat. Off. ........... 514/395

2908627  9/1980  Fed. Rep. of Germany ...... 548/264
3037094  4/1981  Fed. Rep. of Germany .

OTHER PUBLICATIONS

House, Modern Synthetic Reactions, 2nd Edition, pp. 298–303, (1972).
Fieser et al., vol. 8, Reagents for Organic Synthesis, (1980) pp. 10–11, 164–165, 228–229, 504–505.
Buehler et al., Survey of Organic Synthesis, vol. 2, Wiley & Sons (1977) pp. 258–259.
Angewandte Chemie/80.Jahrg. 1968/No. 20, pp. 851 and 852, V. M. Budnowski.

*Primary Examiner*—Glennon H. Hollrah
*Attorney, Agent, or Firm*—Ernest G. Szoke; Henry E. Millson, Jr.

[57] ABSTRACT

A process for the selective production of defined, partial reaction products of polyfunctional N-glycidyl compounds with hydrohalic acids, pseudohydrohalic acids or acids of phosphorus; mono- or di-ring opening products are obtainable as required. The process is carried out at a pH of from about 2 to 10 which is kept constant within a band of at most 2 units on the pH-scale. N,N'-diglycidyl-N"-(halohydroxypropyl)-urazoles and N-glycidyl-N,N"-bis(halohydroxypropyl) urazoles having pharmaceutical utility are produced in good yield.

18 Claims, No Drawings

ACID ADDITION PRODUCTS OF N-GLYCIDYL COMPOUNDS

BACKGROUND OF THE INVENTION

1. Field of the Invention

The invention relates to the preparation of ring-opening products of low molecular weight polyglycidyl compounds wherein at least one of the glycidyl epoxide rings remains intact. In particular, the invention relates to a method for the selective ring opening of polyfunctional N-glycidyl compounds by reaction with a hydrohalic acid, a pseudohydrohalic acid, an acid of phosphorus, or an alkali metal salt of these acids, to provide a ring-opening product retaining a predictable number of glycidyl groups in high yield.

The invention further relates to selected ring-opening products, especially N,N'-diglycidyl-N''-(halohydroxypropyl)-urazoles with iodine or fluorine as the halogen substituent, and N-glycidyl-N',N''-bis-(halohydroxypropyl)-urazoles with fluorine, chlorine, bromine or iodine as the halogen substitutent. The new compounds have utility as antitumor agents in mammals, and the invention accordingly includes pharmaceutical compositions comprising compounds of the invention, and methods for inhibiting tumor growth by administering the compounds to a host mammal.

2. Description of the Prior Art

It is known that polyfunctional glycidyl compounds such as heterocycles containing three or more N-glycidyl groups are reactable with proton acids so that a product wherein only one of the epoxide rings of the glycidyl groups is opened, is obtained. In an exemplary process, described in German patent application No. 30 37 094, a polyfunctional N-glycidyl compound is treated with an excess of acid and the reaction terminated prior to completion. While the reaction product includes the monoaddition product, it is a random mixture comprising the starting compound and compounds wherein one, two, or more glycidyl groups are ring-opened. Pure products containing a specific number of intact glycidyl groups of the type required for pharmaceutical use can only be obtained from these mixtures by arduous separation procedures such as column chromatography or high pressure liquid chromatography. Additionally, the strong acids used in such known processes tend to polymerize the glycidyl compounds. Accordingly, there is an unfulfilled need for a selective ring-opening process which permits one or more of the epoxide rings of polyfunctional N-glycidyl compounds to be predictably opened to provide desired mono-, di-, or polyaddition products in high yield.

DETAILED DESCRIPTION OF THE INVENTION

According to the invention, defined, partial reaction products of polyfunctional N-glycidyl compounds are obtained in high yields by reaction of the N-glycidyl starting material with controlled amounts of a hydrohalic acid, a pseudo hydrohalic acid, an acid of phosphorus, or an alkali metal salt thereof. It has been found that the anion of these acids preferentially adds to the N-glycidyl epoxy rings of the more highly N-glycidyl-substituted reactants in contrast to prior art random acid addition reactions. High yields of a desired ring-opening product are thus obtainable by careful control of process conditions within the parameters of the invention. Exemplary products include the mono- and di-addition products derived from triglycidyl starting materials comprising the corresponding mono- or di-hydroxypropyl derivatives. Polyglycidyl starting materials having at least tetraglycidyl functionality are also specifically contemplated, however. The products are characterized by at least one glycidyl group and one hydroxypropyl substituent per molecule; the anion adds at either the 2 or 3 position of the glycidyl propyl moiety, so that isomeric mixtures are typically produced.

Suitable starting materials for the process of the invention broadly comprise polyfunctional N-glycidyl compounds, i.e. compounds having more than one N-glycidyl group, especially cyclic polyfunctional N-glycidyl compounds containing more than one

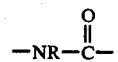

ring group (R is glycidyl). Compounds comprising five-membered or six-membered ring systems, or compounds containing two or more of such five- and/or six-membered ring systems are of particular interest. Typical representatives of preferred starting compounds are polyfunctional N-glycidyl compounds based on urazole, glycoluril, hydantoin, isocyanuric acid, barbituric acid, uric acid or purine. The N-glycidyl substituted starting materials are conveniently obtained by reacting the corresponding NH-compounds with epihalohydrin in known manner, or by other methods well-recognized in the art.

The process according to the invention acquires its surprisingly high selectivity through strict adherence to defined reaction conditions. Thus, the poly-N-glycidyl starting material is reacted with a hydrohalic acid, a pseudohydrohalic acid, an acid of phosphorus, or a sodium, potassium, or lithium salt thereof in aqueous medium at a pH of from about 2 to about 10 and a temperature of from about 0° C. to about 60° C. until a predetermined quantity of epoxide has reacted.

From about 1 to about 20 moles of acid and/or salt are employed per mole of epoxide group to be reacted, with the amount of such excess of acid and/or salt depending upon the reactivity of the anion with the epoxide group. With reactive anions, for example iodide, it is advisable to use equimolar quantities or at most a small excess, whereas with chloride it is preferred to use an approximately 20-fold excess of the anion.

Generally, a mixture of the free acid and an alkali metal salt will be employed, with the ratio of salt to acid depending upon the desired reaction pH. The pH is adjusted and maintained by adding a sufficient quantity of an alkali metal salt of the acid used for ring opening and, if necessary, also a quantity of the acid itself. The reaction is carried out at a pH in the range of from about 2 to about 10, preferably in the range of from about 3 to about 8 and, more preferably, in the range of from about 4 to about 7. It is particularly important in the process of the invention to keep the pH constant within a range of at most 2 pH-units on the pH scale.

In an alternate embodiment, the alkali metal salt, of which the anion is to bring about ring opening, is initially introduced, and the pH kept constant with a foreign acid, of which the anion has comparatively little tendency to add onto the glycidyl groups under the reaction conditions. Sulfuric acid or an organic sulfonic acid are useful foreign acids in this regard. To keep the pH-value constant throughout the entire reaction, such acid is added to the reaction mixture at a rate commensurate with that at which it is consumed by the progressing reaction. The process according to the invention further affords the advantage that the progress of the reaction can also be monitored through the consumption of acid; i.e., the reaction can be terminated when, for example, exactly 1 mole of acid has been consumed per mole of polyfunctional glycidyl compound if a monoaddition product is desired, or, for example, when exactly 2 moles of acid have been consumed per mole of a polyglycidyl (e.g. triglycidyl) compound, if a di-addition product is desired. In the first case, the mono-ring opening product is formed in a high yield; in the second case, the di-ring opening product is formed in high yield. To terminate the reaction, the reaction mixture can be advantageously alkalized, cooled, or the reaction products may be extracted using water-immiscible solvents. On a laboratory scale (i.e., quantities measured in grams), reaction times of from about 1 to about 2 hours were required for producing mono-ring-opened products and reaction times of about 2 to about 3 hours for producing di-ring-opened products. Larger scale reactions may of course require more time for completion.

The reaction takes place at a temperature in the range of from about 0° to about 60° C. The reaction is preferably carried out at temperatures in the range of from about 20° to about 40° C. and, more preferably, at about room temperature. The polyfunctional N-glycidyl starting materials are reacted with the proton acids and/or salts thereof in the presence of water. In cases where the solubility of the starting material is too low to be able to carry out the reaction, i.e., a solubility of, for example, less than about 1 g per 100 g of water, solution-promoting additives can be used. Suitable solution-promoting additives are solvents, solubilizers or surfactants which are inert under the reaction conditions. Thus, it is possible to use alcohols, such as methanol, ethanol and isopropanol; ketones, such as acetone, or amides, such as dimethyl formamide, as solvents, or other solvents selected according to criteria known to those skilled in the art.

In one particularly important embodiment of the invention, the N-glycidyl compound is reacted with a hydrohalic acid and/or an alkali metal halide. In this embodiment, it is preferred to carry out the reaction with mixtures of hydrogen chloride/sodium chloride, hydrogen bromide/sodium bromide or potassium bromide, or hydrogen iodide/potassium iodide. Another embodiment relates to the addition of pseudohydrohalic acids. Pseudohydrohalic acids are understood to be, for example, hydrocyanic acid, cyanic acid and thiocyanic acid. It is particularly preferred to carry out the reaction with their sodium or potassium salts such as, for example, sodium cyanide, sodium cyanate or sodium thiocyanate. In this connection, it is preferred to keep the pH constant by the continuous addition of, for example, sulfuric acid.

In another embodiment of the invention, an acid of phosphorus is employed as reactant. In addition to phosphoric acid and phosphorous acid, suitable acids of phosphorus also include phosphonic acids containing an organic residue, for example hydroxyethylene diphosphonic acid, aminoethylene diphosphonic acid and other monofunctional or difunctional organic phosphonic acids. Where acids of phosphorus are used, it is preferred to carry out the reaction with an acidic salt of the acid or a mixture thereof. Acidic salts of acids of phosphorus are compounds in which at least one acid hydrogen has not been replaced by a metal cation, and at least one acid hydrogen has been replaced by an alkali metal cation. In the case of employing an acid salt of an acid of phosphorous, the pH is also kept constant within the specified range by addition of the corresponding acid.

The reaction products can be worked up in various ways. They may be subjected, for example, to freeze drying and extraction with organic solvents, for example ethers or chlorinated hydrocarbons. However, it is also possible to extract the liquid reaction mixtures with solvents which are immiscible with water. Suitable solvents include chloroform, methylene chloride, diethyl ether or methyl tert.-butyl ether. The reaction products can be further purified by standard methods of organic chemistry, e.g., recrystallization.

In the production of ring-opening products of polyfunctional N-glycidyl compounds according to the invention, the end products are often not chemically uniform, but instead comprise isomer mixtures. Thus, products wherein the acid anion comes in as a substituent in the 3-position of the propyl radical, and the hydroxyl group comes into the 2-position, can be formed; also, however, the isomer wherein the anion is present in the 2-position and the hydroxyl is present in the 3-position on the propyl radical can also be formed. In addition, in cases where the starting compounds do not contain three identical N-glycidyl groups, isomers in which different N-glycidyl groups are ring-opened are generally formed. In any event, however, N-glycidyl compounds containing the required number of opened epoxide rings are almost exclusively obtained. If desired, the individual isomers may be separated by known methods of organic chemistry, for example by standard chromotographic techniques.

The process of the invention is particularly suitable for the production of derivatives of triglycidyl urazole (TGU) with hydrogen chloride, hydrogen bromide or hydrogen iodide, with yields of mono-addition products of more than 50% and typically up to about 79% or more of the theoretical.

To produce addition products of hydrogen fluoride with polyfunctional glycidyl compounds, it is most desirable to produce a corresponding chloro, bromo, or iodo derivative in the manner described above, and to then subject that derivative to a substitution reaction in which the halogen is replaced by fluorine. For example, reaction products of 1,2,4-triglycidyl urazole with hydrogen fluoride are conveniently obtained by reacting that compound with a mixture of sodium chloride and hydrogen chloride in the manner described above, leaving two epoxide groups intact, and then replacing chlorine by fluorine in a conventional substitution reaction.

The halogen substitution reaction is preferably carried out in aprotic dipolar solvents, such as acetonitrile, acetone, butanone, dimethylformamide, dimethyl sulfoxide, hexamethyl phosphoric acid triamide, N-methyl pyrrolidin-2-one, N-formyl piperidine or 1,2-dimethoxyethane. However, the reaction can also be carried out in protic solvents, such as lower ($C_1$–$C_4$) alcohols, or in water, or in mixtures of the above-mentioned solvents. The reaction temperature is preferably in the range of from about 0° to about 100° C. and more preferably in the range of from about 40° to about 80° C. Reactions of this type are well-known, and are more completely described in textbooks of preparative organic chemistry. By means of the above-described substitution process, diglycidyl-(3-fluoro-2-hydroxypropyl)-urazole and other fluoro-substituted urazoles are produced in high yields from the corresponding chloro-substituted compound. Diglycidyl-(3-chloro-2-hydroxypropyl)-isocyanurate is also exemplary of products of the process of the invention. This compound is obtained in typical yields of about 70% of theoretical, and can also be converted into the corresponding fluorine derivative.

Compounds within the scope of the invention which can be produced by the process of the invention comprise the 2,3- and 3,2-halohydroxypropyl isomers of N,N'-diglycidyl-N'-(halohydroxypropyl)-urazoles wherein halo is iodo or fluoro, and N-glycidyl-N',N''-bis(halohydroxypropyl) urazoles, wherein halo is fluoro, chloro, bromo, or iodo. The compounds have utility as antitumor agents. Exemplary new compounds are N,N'-bis(3-bromo-2-hydroxypropyl)-N''-glycidyl urazole and N,N'-diglycidyl-N''-(3-iodo-2-hydroxypropyl)-urazole.

The compounds of the invention are broadly useful as antitumor agents for inhibiting tumor growth in mammals. Pharmaceutical compositions of these compounds with pharmaceutically-acceptable carriers are contemplated for clinical applications. Generally, freshly prepared aqueous solutions of the compounds in a concentration of from about 0.05% to 10% by weight are suitable for pareuteral (i.p. or i.v.) administration. Aqueous carrier systems may suitably include one or more compatible glycol ethers of the type known in the art. The clinical treatment of leukemia and malignant neoplasms such as carcinomas of the lung or colon, melanomas, blastomas, or sarcomas is specifically contemplated. Dosages will vary depending on a variety of factors, including type of tumor, the host mammal, and the compound employed; however, individual dosages between about 1 and about 200 mg/kg will often be efficacious and well tolerated.

The invention is illustrated by the following Examples.

EXAMPLES

1. N,N'-diglycidyl-N''-(3-chloro-2-hydroxypropyl)-urazole

A total of 36.5 g of 10% hydrochloric acid was added dropwise at 40° C. to a solution of 26.9 g (0.1 mole) of 1,2,4-triglycidyl urazole (TGU) in 700 ml of 10% aqueous sodium chloride solution so slowly that the pH-value could be kept constant at pH 5. The addition was over after about 70 minutes. Thereafter the reaction mixture was extracted 4 times with 250 ml of methylene chloride and the methylene chloride distilled off.

After drying in an oil pump vacuum, TLC-pure N,N'-diglycidyl-N''-(3-chloro-2-hydroxypropyl)-urazole, refractive index $n_D^{20}$ 1.5115, was obtained in a yield of 24.2 g (79% of the theoretical).

Epoxide-O: calculated: 10.5%, observed: 10.6%.

The following two compounds were obtained by the same procedure as that used in Example 1 except that HBr was employed in place of HCl and a 10% NaBr solution was used in place of the NaCl solution.

2. N,N'-diglycidyl-N''-(3-bromo-2-hydroxypropyl)-urazole

HBr dropwise addition time: 65 minutes, $n_D^{20}$: 1.5183, epoxide O: calculated: 9.2%, observed: 8.8%.

3. N-glycidyl-N'N''-bis(3-bromo-2-hydroxypropyl)-urazole (new)

HBr dropwise addition time: 150 minutes, $n_D^{20}$: 1.5342, epoxide O: calculated 3.7%, observed: 3.8%.

4. N,N'-diglycidyl-N''-(3-iodo-2-hydroxypropyl)-urazole (new)

6.4 g (0.05 moles) of 10% hydriodic acid were added dropwise with stirring at 40° C. to a solution of 13.5 g (0.05 mole) of TGU and 7.5 g (0.05 mole) of sodium iodide in 300 ml of water at such a rate that the pH-value stayed at around 5. The addition was over after about 13 minutes. After working up in the manner described in Example 1 above, TLC-pure, colorless N,N'-diglycidyl-N''-(3-iodo-2-hydroxypropyl)-urazole, refractive index $n_D^{20}$ 1.5450, was obtained in a yield of 18.5 g (94% of the theoretical).

Epoxide-O: calculated: 8.1%, observed: 7.8%.

5. Diglycidyl-(3-chloro-2-hydroxypropyl)-isocyanurate (cf. German patent application No. 30 37 094.6)

9 g of 10% hydrochloric acid were added dropwise to a solution of 7.42 g (0.025 mole) of triglycidyl isocyanurate and 1.45 g (0.025 mole) of sodium chloride in 200 ml of water at such a rate that the pH-value stayed between 6 and 8. After the hydrochloric acid had been added (65 minutes), the reaction mixture was worked up in the same way as in Example 1 above. Diglycidyl-(3-chloro-2-hydroxypropyl)-isocyanurate was obtained as a TLC-pure (identical with a known sample) colorless, viscous oil in a yield of 6.4 g (77% of the theoretical).

Epoxide-O: calculated: 9.6%, observed: 9.0%.

The compounds produced in accordance with Examples 1 to 5 were found to be uniform by thin-layer chromatography (eluent methylene chloride : ethylacetate : methanol 3:2:1, solid phase Keiselgel (silica gel) 60 (e. Merck, Darmstadt, Federal Republic of Germany).

6. 1,2-diglycidyl-4-(3-fluoro-2-hydroxypropyl)-urazole (new)

2.1 g (50 mMoles of sodium fluoride were added to a solution of 1.5 g (5 mMoles) of 1,2-diglycidyl-4-(3-chloro-2-hydroxypropyl)-urazole in 100 ml of acetone and the mixture boiled for 6 hours. After the solvent had been distilled off and the residue taken up in 50 ml of methylene chloride, followed by filtration, removal of the methylene chloride by distillation and drying in an oil pump vacuum at 40° C., 1,2-diglycidyl-4-(3-fluoro-2-hydroxypropyl)-urazole, refractive index $n_D^{20}$:1.4955 (colorless liquid), was obtained in a yield of 1.5 g (100%).

Epoxide-O: 10.9 observed, 11.1 calculated. F: 6.0 observed, 6.6 calculated.

The efficacy and toxicity of this compound as an antitumor agent is summarized in the data set forth in the Table, Ex. 8, infra.

7. Monoadduct of dipotassium hydrogen phosphate with 1,2,4-triglycidyl urazole (1:1-adduct)

26.9 g (0.1 mole) of 1,2,4-triglycidyl urazole (TGU) and 17.4 g (0.1 mole) of dipotassium hydrogen phosphate were dissolved in 240 ml of water and the resulting solution heated to 60° C. 26 ml of 10% phosphoric acid were added over a period of 3 hours during which the pH-value was kept at 8.0 (plus/minus 0.5). On completion of the reaction, the reaction mixture was cooled to 20° C. and extracted with methylene chloride to remove unreacted TGU. The aqueous solution was then freeze-dried. 47.7 g of the 1:1-adduct having a residual water content of 4% were obtained.

Free phosphate as P: 2%.
Epoxide-oxygen: observed: 6.3%, calculated: 6.6%.

8. Efficacy as antitumor agents

The following tests were carried out in accordance with the procedures set forth by the National Cancer Institute, Bethesda, Md. 200014, as published in "Cancer Chemotherapy Reports" Part 3, September, 1972, Vol. 3, No. 2.

Type P 388 tumor (leukaemia) was introduced i.p. into mice in accordance with Protocol 1200 (page 91c) in a quantity sufficient to produce $10^6$ cells per mouse. The average survival time of the animals was determined.

Efficacy and toxicity of compounds according to the invention was evaluated by administering the compounds i.p. to a test group of mice inoculated with type P 388 tumor, and comparing survival time of the mice in the test group with survival time of a control group of mice, in accordance with NCI guidelines. Percent prolongation of survival time of animals in the test group as compared to animals in the control group is expressed as a value T/C.

Test results are summarized in the following Table. Tested compounds comprised adducts of various mineral acids as indicated in the Table with triglycidyl isocyanurate (TGU), and 1,2-diglycidyl-4-(3-fluoro-2-hydroxypropyl) urazole. The substances were freshly prepared in the form of aqueous, 1% injection solutions immediately before application.

In all instances, the life of the test animals treated in accordance with the invention was significantly prolonged by comparison with the average survival period of the control animals. The prolongation value T/C was dependent upon the dosage of the active ingredient is shown in the following Table:

TABLE TO EXAMPLE 8

| Reaction product of 1 mole of TGU with: | Measured T/C-values (%) Dose administered i.p. (mg/kg) | | | | |
|---|---|---|---|---|---|
| | 30 | 50 | 60 | 120 | 240 |
| 1 mole of HCl | — | 283 | — | toxic | toxic |
| 1 mole of HBr | — | 238 | — | 93 | toxic |
| 2 moles of HBr | — | 117 | — | 180 | 228 |
| 1 mole of HI | — | 155 | — | 200 | 285 |
| 1 mole of NaH$_2$PO$_4$ | — | 113 | — | 137 | 141 |
| 1,2-diglycidyl-4-(3-fluoro-2-hydroxy-propyl)-urazole (Example 6) | 182 | — | 202 | 272 | toxic |

What is claimed is:

1. A process for the production of a reaction product of a poly-N-glycidyl compound having at least one five-membered or six-membered heterocyclic ring system containing at least two

groups in the ring thereof, wherein R is glycidyl, and wherein said reaction product contains at least one N-glycidyl substituent comprising reacting said poly-N-glycidyl compound with a free acid comprising a hydrohalic acid, a pseudohydrohalic acid, or an acid of phosphorus; an alkali metal salt of said free acid; or a mixture of said free acid and said alkali metal salt; in an amount of from about 1 to about 20 moles of acid, salt, or mixture thereof per mole of N-glycidyl compound in aqueous medium at a reaction temperature of from about 0° C. to about 60° C. at a reaction pH of from about 2 to about 10 within a range of at most about 2 units on the pH scale for a period of time sufficient to provide a ring-opened addition product containing at least one N-glycidyl substituent and at least one hydroxypropyl substituent substituted with the anion of said acid or said salt wherein said addition product is obtained in a yield of at least 50% of the theoretical yield.

2. The process of claim 1, wherein a mono-addition product is obtained in a yield of at least about 50% of theoretical.

3. The process of claim 1, wherein a di-addition product is obtained in a yield of at least about 50% of theoretical.

4. The process of claim 1, wherein said N-glycidyl compound is 1,2,4-triglycidyl urazole.

5. The process of claim 1, wherein said N-glycidyl compound contains at least three glycidyl substituents, and said addition product contains two N-glycidyl substituents per molecule.

6. The process of claim 1, wherein said N-glycidyl compound is an N-glycidyl derivative of urazole, glycoluril, hydantoin, isocyanuric acid, barbituric acid or uric acid.

7. The process of claim 1, wherein the hydrohalic acid is hydrochloric acid, hydroiodic acid, or hydrobromic acid, and the pseudohydrohalic acid is hydrocyanic acid, cyanic acid or thiocyanic acid.

8. The process of claim 1, wherein the alkali metal salt is a lithium, sodium, or potassium salt.

9. The process of claim 1, wherein the alkali metal salt of said acid of phosphorus is an acidic salt.

10. The process of claim 7, wherein the alkali metal salt of the pseudohydrohalic acid is a sodium or potassium salt.

11. The process of claim 1, wherein the acid of phosphorus is a phosphoric acid, a phosphorous acid, or a phosphonic acid having an organic residue.

12. The process of claim 1, wherein the reaction pH is regulated by addition of said acid to the reaction medium at a rate commensurate with the rate of consumption of the acid.

13. The process of claim 1, wherein at least an equimolar amount of said alkali metal salt of said free acid is initially introduced into the reaction medium, and the pH of the reaction is then regulated by addition of said free acid.

14. The process of claim 13, wherein the addition of the free acid is substantially continuous.

15. The process of claim 1, wherein the reaction temperature is from about 20° to about 40° C.

16. The process of claim 1, wherein the reaction pH is from about 3 to about 8.

17. The process of claim 1, wherein the reaction pH is from about 4 to about 7.

18. The process of claim 1, wherein said alkali metal salt has a substantially neutral reaction in aqueous solution.

* * * * *